United States Patent
Economou et al.

(10) Patent No.: US 10,300,020 B2
(45) Date of Patent: *May 28, 2019

(54) FORMULATION AND MANUFACTURING PROCESS FOR CALCIUM ACETATE CAPSULES

(71) Applicant: West-Ward Pharmaceuticals International Limited, London (GB)

(72) Inventors: Julie Economou, Dublin, OH (US); Shehla Uraizee, Dublin, OH (US)

(73) Assignee: WEST-WARD PHARMACEUTICALS INTERNATIONAL LIMITED, London (GB)

(*) Notice: Subject to any disclaimer, the term of this patent is extended or adjusted under 35 U.S.C. 154(b) by 65 days.

This patent is subject to a terminal disclaimer.

(21) Appl. No.: 14/541,819

(22) Filed: Nov. 14, 2014

(65) Prior Publication Data

US 2015/0071996 A1 Mar. 12, 2015

Related U.S. Application Data

(60) Continuation of application No. 14/027,650, filed on Sep. 16, 2013, now Pat. No. 9,060,951, and a division of application No. 11/566,938, filed on Dec. 5, 2006, now Pat. No. 8,563,032.

(60) Provisional application No. 60/742,502, filed on Dec. 5, 2005.

(51) Int. Cl.

| A61K 9/48 | (2006.01) |
|---|---|
| A61K 9/16 | (2006.01) |
| A61K 31/19 | (2006.01) |
| A61K 9/14 | (2006.01) |

(52) U.S. Cl.
CPC .............. *A61K 9/4833* (2013.01); *A61K 9/14* (2013.01); *A61K 9/1635* (2013.01); *A61K 9/1688* (2013.01); *A61K 9/48* (2013.01); *A61K 31/19* (2013.01)

(58) Field of Classification Search
CPC .................................... A61K 9/14; A61K 9/48
See application file for complete search history.

(56) References Cited

U.S. PATENT DOCUMENTS

| 4,017,424 A | 4/1977 | Johnson et al. |
|---|---|---|
| 4,071,331 A | 1/1978 | Johnson et al. |
| 4,140,493 A | 2/1979 | Johnson et al. |
| 4,508,893 A | 4/1985 | Koyama et al. |
| 4,609,675 A | 9/1986 | Frazn |
| 4,870,105 A | 9/1989 | Fordtran |
| 5,347,046 A | 9/1994 | White et al. |
| 5,603,971 A | 2/1997 | Porzio et al. |
| 5,641,510 A * | 6/1997 | Clark ...................... A61J 3/071 424/451 |
| 5,767,107 A | 6/1998 | Chaundy et al. |
| 5,897,897 A | 4/1999 | Porzio et al. |
| 6,187,351 B1 | 2/2001 | Porzio et al. |
| 6,201,053 B1 | 3/2001 | Dieckmann et al. |
| 6,576,665 B2 | 6/2003 | Dennett, Jr. et al. |
| 6,875,445 B2 | 4/2005 | Dennett, Jr. et al. |
| 2003/0050340 A1 | 3/2003 | Dennett, Jr. et al. |

FOREIGN PATENT DOCUMENTS

| EP | 0237345 | 9/1987 |
|---|---|---|
| JP | 04235942 | 1/1991 |

OTHER PUBLICATIONS http://www.accessdata.fda.gov/scripts/cder/drugsatfda/index.cfm?fus . . . , Label and Approval History for PHOSLO GELCAPS, Jul. 1, 2014.
Lightfoot et al., Capsule Filing: Answers to 10 Common Questions about Capsule Filling, Tablets & Capsules, CSC Publishing.

* cited by examiner

*Primary Examiner* — Kyle A Purdy
(74) *Attorney, Agent, or Firm* — Pearne & Gordon LLP

(57) ABSTRACT

The present invention relates to a pharmaceutical calcium acetate formulation and a process for making the same. In particular, the present invention relates to a calcium acetate capsule formulation comprising granules comprising calcium acetate along with other formulation adjuvants contained within a pharmaceutically acceptable capsule.

15 Claims, 1 Drawing Sheet

FLOW DIAGRAM OF THE MANUFACTURING PROCESS
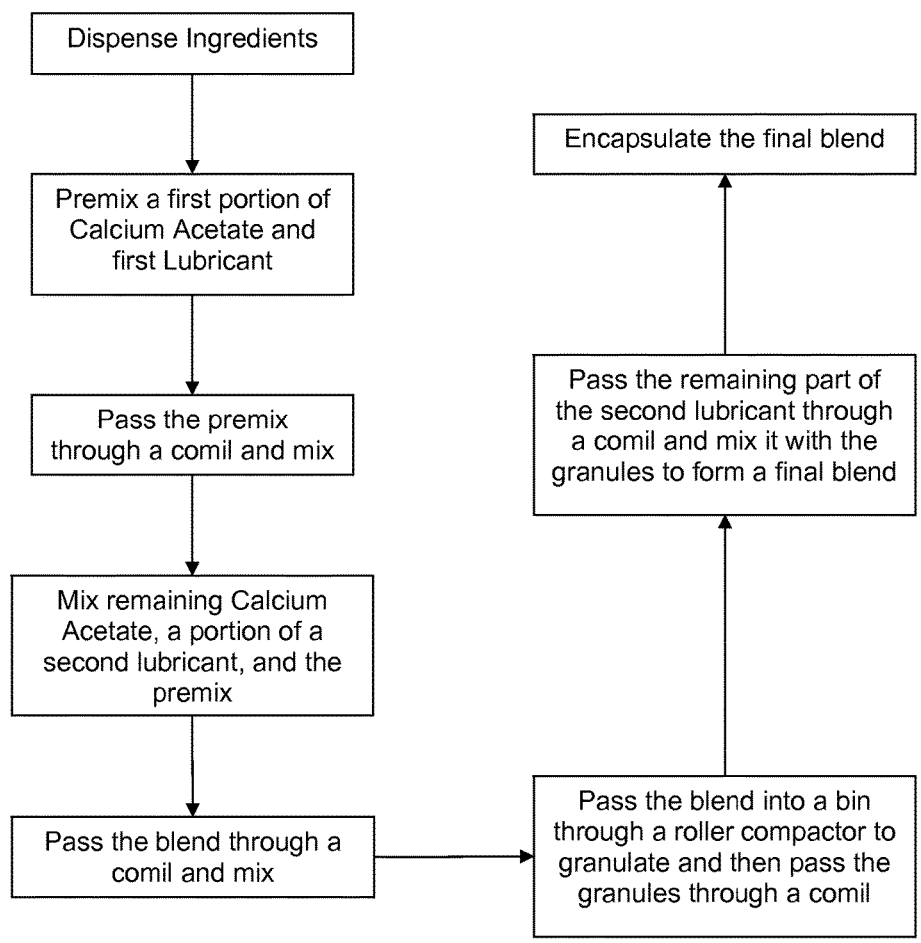

FORMULATION AND MANUFACTURING PROCESS FOR CALCIUM ACETATE CAPSULES

This application is a continuation of U.S. patent application Ser. No. 14/027,650 filed Sep. 16, 2013, which is a divisional of U.S. patent application Ser. No. 11/566,938, filed Dec. 5, 2006, now U.S. Pat. No. 8,563,032, which claims the benefit of the filing date of U.S. Provisional Application No. 60/742,502, filed on Dec. 5, 2005, which is incorporated herein by reference in its entirety.

FIELD OF THE INVENTION

The present invention relates to a pharmaceutical calcium acetate formulation and a process for making the same. In particular, the present invention relates to a calcium acetate capsule formulation comprising granules comprising a pharmaceutically acceptable amount of calcium acetate along with other formulation adjuvants contained within a pharmaceutically acceptable capsule.

BACKGROUND OF THE INVENTION

In the pharmaceutical industry, there are many pharmaceutical products which are difficult to manufacture into palatable dosage forms due to the intrinsic properties of the active ingredient. For example, many pharmaceutically active ingredients have properties which are such that in order to formulate a single dose, large quantities must be used. Accordingly, either multiple doses must be taken or single dose forms are large in size making them difficult to swallow. Additionally, many pharmaceutically active compounds are unpleasant tasting which, in turn, limits the forms in which they can be produced to alleviate this property.

Phosphorous binders bind phosphorus in the form of a phosphorous ion within the stomach and intestines and are useful in the treatment of patients with chronic renal disease. This process is thought to result from a chemical reaction between dietary phosphorus and the cation present in the binder compound. The reaction causes the formation of insoluble and hence unabsorbable phosphate compounds. The cation in some phosphorous binders is aluminum or calcium. Despite their capacity for binding phosphorous, large quantities of antacids must be ingested over a long period of time for them to be effective. Therefore, dosage size and palatability are particularly important for patients with chronic renal disease.

Calcium acetate is a particularly effective medication which is commonly used in the treatment of chronic renal failure, or hyperphosphatemia. Calcium acetate binds phosphorus in the gastrointestinal tract and reduces the percentage of consumed phosphorus which is absorbed into the bloodstream. Calcium acetate is particularly effective in reducing phosphorous absorption when it is administered relatively close in time to food consumption. Calcium acetate is typically administered orally. However, one common drawback to conventional calcium acetate formulations is that calcium acetate, like many other antacids, has an unpleasant, chalky taste.

Calcium acetate had been traditionally formulated as tablets. However, the tablet form of calcium acetate does little to enhance the palatability of the active compound. Attempts to address this concern include encapsulation of caplets of the calcium acetate as disclosed in U.S. Pat. Nos. 6,576,665 and 6,875,445. These patents also relate to a specific useful bulk density of the calcium acetate as being from 0.55-0.75 g/cc.

Current calcium acetate formulations on the market include PHOSLO Gelcaps which comprise a 667 mg dose of calcium acetate manufactured as caplets placed inside a capsule shell (Size 0). However, the process which is used to generate the encapsulated caplets involves both a tablet forming step to formulate the caplet and special equipment to encase the caplet in an outer capsule. Accordingly, a simplified, more efficient process, compared to the process for producing the encapsulated caplet formulation, which produces a calcium acetate product that provides an effective dose of the active product without the unpleasant taste associated with the calcium acetate active substance, would be desirable.

SUMMARY OF THE INVENTION

The present invention comprises capsules filled with granules of calcium acetate. More specifically, the present invention relates to a calcium acetate capsule formulation comprising granules wherein the granules are comprised of a pharmaceutically acceptable amount of calcium acetate along with other formulation adjuvants contained within a pharmaceutically acceptable capsule.

According to one aspect of the invention, the bulk density of the calcium acetate used in the formulation according to the present invention is typically less than about 0.55 g/cc. In a further embodiment, the bulk density of the calcium acetate is between about 0.30 g/cc to less than about 0.55 g/cc. In a further embodiment, the calcium acetate has a bulk density of less than about 0.50 g/cc. In yet another embodiment, the calcium acetate has a bulk density of less than about 0.45 g/cc. In a further embodiment, the calcium acetate has a bulk density of from about 0.30 g/cc to about 0.45 g/cc.

According to another aspect of the invention, calcium acetate is formulated with various adjuvants to aid in the filling of the capsules. In particular, various glidants and lubricants may be added to the calcium acetate to improve flowability of the powder blend.

According to another aspect of the invention, a blend of calcium acetate and formulation adjuvants is granulated to aid in the filling of the capsules. The granulation can be achieved through the use of granulation equipment such as a roller compactor. In a further aspect of the invention, granulation of the calcium acetate results in the final blend having a median particle size of from about 450 microns to about 600 microns. According to another aspect of the invention, a blend of calcium acetate and formulation adjuvants are sized such that about 75% of the particles are retained on a 150 micron sieve.

Another aspect of the invention is directed to a process for encapsulation of granulated calcium acetate. A further aspect of the invention relates to a process for manufacturing capsules comprising calcium acetate wherein the process comprises the steps of:

a) blending a portion of a pharmaceutically acceptable amount of calcium acetate and a first lubricant, such as polyethylene glycol, and then passing the blend through a mill to deagglomerate the blend and then mixing the deagglomerated blend to form a first blend;

b) adding to the first blend, the remaining portion of the pharmaceutically acceptable amount of the calcium acetate to a portion of a pharmaceutically acceptable amount of a second lubricant, such as magnesium stearate, NF, blending and mixing to form a second blend;

c) passing the second blend of step b) through a mill to deagglomerate the second blend and mixing again;

d) granulating the second blend of step c) using a roller compactor to form a granulated product;

e) passing the granulated product of step d) through a comil to size the granules to a pharmaceutically acceptable size;

f) adding the second blend and the remaining pharmaceutically acceptable amount of the second lubricant, e.g., magnesium stearate, and blending to form a final blend;

g) filling the final blend of step f) into capsules using an encapsulation device.

Advantages of this process include, but are not limited to the following: (1) The process of the invention requires no additional purchase or modification of existing conventional capsule manufacturing equipment, (2) the process is simple and less time consuming than the caplet/capsule process described in the prior art literature (i.e. compression into tablets or caplets is not needed), and (3) the bulk density of the calcium acetate can be lower than that required by the prior art and is not restricted to the particular range recited in the patent literature.

BRIEF DESCRIPTION OF THE DRAWING

The FIGURE is a flow diagram which depicts an example of the manufacturing process used to make the calcium acetate capsules of the invention.

DETAILED DESCRIPTION OF THE INVENTION

The present invention comprises the production of calcium acetate capsules. The calcium acetate capsules of the invention are formulated by filling a pharmaceutically acceptable capsule with granules comprised of calcium acetate and other formulation adjuvants. According to one embodiment of the invention, the capsule is a size 00 capsule containing 667 mg of calcium acetate. Capsules containing smaller doses of calcium acetate can be sized accordingly using smaller capsules.

The bulk density of the calcium acetate used in the invention was measured in accordance with USP <616>, Method I. According to USP <616>, the bulk density is determined by measuring the volume of a known mass of powder that has been passed through a screen into a graduated cylinder. The bulk density of the calcium acetate used in the granulated formulation of the invention is less than about 0.55 g/cc and preferably less than about 0.45 g/cc. In another preferred embodiment, the bulk density is between about 0.30 g/cc to about less than 0.55 g/cc. More preferably the bulk density is between about 0.30 g/cc to about 0.45 g/cc.

A further aspect of the calcium acetate is that it has a tap density of from about 0.45 g/cc to about 0.65 g/cc. In one embodiment, the tap density of the calcium acetate is about 0.60 g/cc. The tap density was measured in accordance with USP <616>, Method II. According to USP <616>, the tapped density is achieved by mechanically tapping a measuring cylinder containing a powder sample. After observing the initial volume, the cylinder is mechanically tapped and volume readings are taken until little further volume change is observed. The mechanical tapping is achieved by raising the cylinder containing the sample and allowing it to drop under its own weight a specified distance according to one of two methods (Method I and II as outlined in the USP). According to USP <616>, Method II, for tapped density, a mechanical tapped density tested is used which provides a fixed drop of the cylinder of 3 mm (±10%) at a nominal rate of 250 drops per minute.

In order to be able to fill the capsules using a capsule filling machine, for example an IMA, at a rate that would be commercially viable, the drug, along with other formulation adjuvants, is formulated into a final blend which is then granulated. According to one aspect of the invention, the calcium acetate and other formulation adjuvants are granulated using a roller compactor. Other granulation processes including, but not limited to, high shear, low shear and fluidized bed technology, can be used in place of roller compaction. Granulation of the calcium acetate and other adjuvants is conducted such that the calcium acetate final blend has a median particle size of from about 450 microns to about 600 microns. According to another aspect of the invention, a blend of calcium acetate and formulation adjuvants are sized such that about 75% of the particles are retained on a 150 micron sieve.

Pharmaceutically acceptable adjuvants include, but are not limited to, disintegrants, diluents, lubricants, glidants, and blends thereof. Glidants and lubricants may be added to a formulation to improve the flowability of a powder blend, reduce powder adhesion to equipment, and to improve the consistency of dosage weight. In particular, calcium acetate having a bulk density of between about 0.30 g/cc to less than about 0.55 g/cc was found to have flowability problems when attempting to fill capsules with the active calcium acetate alone. According to the invention, it has been found that incorporation of adjuvants, such as lubricants and/or glidants in the formulation and granulating the formulation addresses the flowability issues so that economical and efficient manufacture of calcium acetate capsules is achieved. Adjuvants that may function as glidants include colloidal silicon dioxide, magnesium silicate, powdered cellulose, starch, talc and tribasic calcium phosphate, and mixtures thereof. Lubricants include magnesium stearate, calcium stearate, glyceryl monostearate, glyceryl palmitostearate, glyceryl behenate, hydrogenated castor oil, hydrogenated vegetable oil, mineral oil, polyethylene glycol, sodium benzoate, sodium lauryl sulfate, sodium stearyl fumarate, stearic acid, talc, zinc stearate, and mixtures thereof.

An exemplary, but non-limiting, formulation and process for manufacturing the same are described in detail below:

Formulation:

| Calcium Acetate Capsules, 667 mg | Quantitative Composition (mg/capsule) |
|---|---|
| Calcium Acetate, USP (Powder) | 710 * |
| Polyethylene Glycol 8000, NF (Carbowax 8000) | 38.6 |
| Magnesium Stearate, NF | 11.4 |
| Theoretical Capsule Fill Weight (mg) | 760 |

* The water content specification for calcium acetate USP (Powder) is 5.0-7.0%. Based on 6% w/w water content, 710 mg of calcium acetate, USP (Powder) is equivalent to 667 mg of calcium acetate on an anhydrous basis. Since the water content range of calcium acetate, USP (Powder) is narrow (5.0-7.0%), the assay values of the finished product are expected to range from 99-101% of the labeled amount. Therefore, no adjustments are made in the formulation to accommodate for the lot to lot variation in the water content.

Manufacturing Process:

According to the invention, a process for manufacturing the encapsulated granulated calcium acetate consists of the following steps:

a) blending a portion of a pharmaceutically acceptable amount of calcium acetate and a first lubricant, such as polyethylene glycol, and then passing the blend through a mill to deagglomerate the blend and then mixing the deagglomerated blend to form a first blend;
b) adding to the first blend, the remaining portion of the pharmaceutically acceptable amount of the calcium acetate to a portion of a pharmaceutically acceptable amount of a second lubricant, such as magnesium stearate, NF, blending and mixing to form a second blend;
c) passing the second blend of step b) through a mill to deagglomerate the second blend and mixing again;
d) granulating the second blend of step c) using a roller compactor to form a granulated product;
e) passing the granulated product of step d) through a comil to size the granules to a pharmaceutically acceptable size;
f) adding the second blend and the remaining pharmaceutically acceptable amount of the second lubricant, e.g., magnesium stearate, and blending to form a final blend;
g) filling the final blend of step f) into capsules using an encapsulation device.

Advantages of this process include, but are not limited to the following: (1) The process of the invention requires no additional purchase or modification of existing conventional capsule manufacturing equipment, (2) the process is simple and less time consuming than the caplet/capsule process described in the prior art literature (i.e. compression into tablets or caplets is not needed), and (3) the bulk density of the calcium acetate can be lower than that required by the prior art and is not restricted to the particular range recited in the patent literature.

The following Example is representative of the process for making the encapsulated granulated calcium acetate product of the invention:

EXAMPLE 1

Capsules of calcium acetate containing a 667 mg dose of the active calcium acetate ingredient, having a bulk density of 0.47 g/cc, were prepared according to the following process:

In an 8 L bin, 1.211 kg of calcium acetate was added along with 1.211 kg of Carbowax 8000 (a polyethylene glycol). The components were then blended at a speed of 45 rpm for 120 revolutions. The mixture was then passed through a comil equipped with a 0.055 inch round screen at a speed of 608 rpm to form a first blend. In a separate 100 L bin, 17.326 kg of calcium acetate was added along with 0.084 kg magnesium stearate and the first blend of materials. This mixture was then blended at a speed of 13 rpm for 120 revolutions. This mixture was then passed through a comil equipped with a 0.055 inch round screen at a speed of 608 rpm. The milled mixture was then blended again in a bin blender at a speed of 13 rpm for 120 revolutions to form a second blend. The second blend was then passed through a roller compactor having a breaker rpm of 100 rpm and a hydraulic pressure of 30 Bar to granulate the second blend. The granulated second blend was then passed through a comil having a 0.040 inch grater screen at a speed of 608 rpm. The second blend was then mixed with 101 g of magnesium stearate (which had been passed through a comil having a grater screen size of 0.05 inches) and blended at 16 rpm for 60 revolutions to form a final blend. The final blend was then filled into size 00 capsules using an IMA capsule filling machine wherein the resulting filled capsules had a weight of 880 mg and contained 760 mg of the final blend, including a 667 mg dose of calcium acetate.

Calcium acetate capsules produced in accordance with the invention were tested for dissolution in water. In a first series of tests, the dissolution of the calcium acetate from 6 capsules after 10 minutes was at least 86% with at least 96% dissolution at 15 minutes.

TABLE 1

| | % LA (Labeled Amount) (667 mg Capsules) | | | | | |
|---|---|---|---|---|---|---|
| | 1 | 2 | 3 | 4 | 5 | 6 |
| 10 min | 87 | 96 | 102 | 93 | 94 | 86 |
| 15 min | 105 | 101 | 99 | 100 | 104 | 96 |

In a second series of tests, the dissolution of calcium acetate from 6 capsules was at least 95% at 10 minutes with complete dissolution at 15 minutes.

TABLE 2

| | % LA (667 mg Capsules) | | | | | |
|---|---|---|---|---|---|---|
| | 1 | 2 | 3 | 4 | 5 | 6 |
| 10 min | 117 | 109 | 96 | 117 | 104 | 95 |
| 15 min | 106 | 105 | 107 | 110 | 120 | 102 |

As can be seen from the above examples, the calcium acetate capsules containing granulated calcium acetate were able to be produced using conventional granulation and encapsulating equipment and procedures wherein the resulting products have dissolution rates which are acceptable for immediate release formulations of calcium acetate.

While various embodiments in accordance with the present invention have been shown and described, it is understood the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A capsule containing a calcium acetate formulation comprising flowable granules, the flowable granules being comprised of calcium acetate and an adjuvant, and the flowable granules being granulating a dry blend comprising calcium acetate and an adjuvant under pressure in a roller compactor, wherein the flowable granules comprise a tap density, the tap density being such that 667 mg of the calcium acetate on an anhydrous basis of the flowable granules can be filed into a size 00 capsule.

2. The capsule of claim 1, the granules being granulated under hydraulic pressure.

3. The capsule of claim 1, the adjuvant being a lubricant, glidant, disintegrants or diluents.

4. The capsule of claim 3, the adjuvant being polyethylene glycol.

5. The capsule of claim 3, the adjuvant being magnesium stearate.

6. The capsule of claim 1, the flowable granules not being compressed into a tablet or caplet before being filled into the capsule.

7. The capsule of claim 1, the flowable granules being filled into the capsule using an encapsulation device.

8. The capsule of claim 1, the capsule containing 667 mg of calcium acetate on an anhydrous basis.

9. The capsule of claim 1, the capsule being size 00.

10. The capsule of claim 1, the capsule having a dissolution in water such that at least 86% of the calcium acetate is dissoluted within 10 minutes.

11. The capsule of claim 1, the capsule having a dissolution in water such that at least 96% of the calcium acetate is dissoluted within 15 minutes.

12. The capsule of claim 1, the capsule having a dissolution in water such that at least 95% of the calcium acetate is dissoluted within 10 minutes.

13. The capsule of claim 1, the capsule having a dissolution in water such that at least 100% of the calcium acetate is dissoluted within 15 minutes.

14. The capsule of claim 1, the flowable granules having a median particle size of from about 450 microns to about 600 microns.

15. The capsule of claim 1, the flowable granules being sized such that about 75% of the particles are retained on a 150 micron sieve.

* * * * *